(12) United States Patent
Lam

(10) Patent No.: US 11,896,725 B2
(45) Date of Patent: Feb. 13, 2024

(54) PORTABLE BAG FOR STERILIZING AN OBJECT

(71) Applicant: Juladore Limited, London (GB)

(72) Inventor: Hiu Ying Lam, Taipo (HK)

( * ) Notice: Subject to any disclaimer, the term of this patent is extended or adjusted under 35 U.S.C. 154(b) by 0 days.

(21) Appl. No.: 17/051,994

(22) PCT Filed: May 28, 2020

(86) PCT No.: PCT/CN2020/092783
§ 371 (c)(1),
(2) Date: Oct. 30, 2020

(87) PCT Pub. No.: WO2021/232462
PCT Pub. Date: Nov. 25, 2021

(65) Prior Publication Data
US 2023/0098354 A1 Mar. 30, 2023

(30) Foreign Application Priority Data
May 20, 2020 (HK) .......................... 32020007824.6

(51) Int. Cl.
*A61L 2/10* (2006.01)
*A61L 2/24* (2006.01)

(52) U.S. Cl.
CPC .................. *A61L 2/10* (2013.01); *A61L 2/24* (2013.01); *A61L 2202/14* (2013.01); *A61L 2202/16* (2013.01)

(58) Field of Classification Search
CPC .......... A61L 2/10; A61L 2/24; A61L 2202/14; A61L 2202/16; A61L 2202/122;
(Continued)

(56) References Cited

U.S. PATENT DOCUMENTS 6,513,661 B1 * 2/2003 Mogil .................. A63B 55/408
150/112
2014/0265039 A1 * 9/2014 Bellec ................. B29C 49/4252
264/405
(Continued)

FOREIGN PATENT DOCUMENTS

CN 203137369 U * 8/2013
CN 203137369 U 8/2013
(Continued)

OTHER PUBLICATIONS

International Search Report; PCT/CN2020/092783; May 28, 2020 Int. Filing Date; May 20, 2020 earliest priority date; dated Feb. 24, 2021 mailing date.
(Continued)

*Primary Examiner* — Michael Maskell (57) ABSTRACT

The invention relates to portable bag for sterilizing an object accommodated therein. The portable bag comprises a flexible body defining an internal space for accommodating the object; a plurality of ultraviolet (UV) radiation emitting means arranged at opposing internal walls of the flexible body; wherein the flexible body comprises one or more layers of fabric material, with one layer of the one or more layers forming the internal walls comprising a reflective fabric material adapted to reflect ultraviolet (UV) radiation emitted from the UV radiation emitting means and UV radiation reflected from the object. The invention further relates to a method of manufacturing said portable bag.

19 Claims, 10 Drawing Sheets

(58) Field of Classification Search
CPC .. A61L 2202/181; A61L 2/26; A61L 2202/26; A45C 11/00; A45C 2011/007; A45C 11/008; A45C 15/00; A45C 3/001; A45C 15/06; A45C 2003/008
USPC .......................................... 250/504 R, 455.11
See application file for complete search history.

(56) References Cited

U.S. PATENT DOCUMENTS

| | | | | |
|---|---|---|---|---|
| 2015/0297768 | A1* | 10/2015 | Bettles | A61L 2/10 250/455.11 |
| 2018/0214585 | A1* | 8/2018 | Piper | A61L 2/0047 |
| 2020/0254121 | A1* | 8/2020 | Swaney | A61L 2/10 |
| 2021/0379219 | A1* | 12/2021 | Hariri | A61L 2/10 |
| 2022/0031884 | A1* | 2/2022 | Whyte | A61L 2/26 |

FOREIGN PATENT DOCUMENTS

| | | | | | |
|---|---|---|---|---|---|
| CN | 105167366 | A | | 12/2015 | |
| CN | 205019463 | U | * | 2/2016 | |
| CN | 205667417 | U | | 11/2016 | |
| CN | 206026884 | U | | 3/2017 | |
| CN | 107823676 | A | * | 3/2018 | |
| CN | 209060064 | U | | 5/2019 | |
| CN | 210353589 | U | | 4/2020 | |
| CN | 210542542 | U | | 5/2020 | |
| CN | 113633086 | A | * | 11/2021 | |
| WO | WO-2013104013 | A1 | * | 7/2013 | ............. A45C 15/06 |

OTHER PUBLICATIONS

Search Report issued by CNIPA on Hong Kong Short Term pat. appln.

* cited by examiner

PORTABLE BAG FOR STERILIZING AN OBJECT

FIELD OF THE INVENTION

The invention relates to a portable bag for sterilizing an object accommodated therein, and particularly but not exclusively, to a portable bag for sterilizing the object via ultraviolet irradiation.

BACKGROUND OF THE INVENTION

Various technologies have been developed with an aim to enhance personal and environmental hygiene and to prevent spreading of diseases in society. Despite the increasing awareness of the need to exercise higher standards of hygiene practices, many everyday items and/or personal items such as mobile phones, wallets, card holders, keys or even bank notes and coins, etc. are known to become heavily contaminated with harmful germs such as bacteria and viruses. One ordinary way to sanitize or disinfect these items is for the user to manually and regularly clean or wash the items with cleaning agents such as soap water, bleach solution or the like. However, it will be understood that common cleaning agents may be effective to destroy only certain types or limited amounts of the pathogens, and that the cleaning steps and the agents used may not always be compatible with the materials or the structures of the items requiring sanitization or sterilization. The cleaning procedure might also be inconvenient to be carried out by the user, especially when the cleaning is required to be conducted outdoors or when the user is travelling. The effectiveness of manual cleaning may also be highly dependent on the appropriateness of the cleaning steps and, more particularly, the thoroughness of the cleaning, and therefore, a desirable hygiene level might not be easily controllable or achievable.

In view of the drawbacks and difficulties of manual disinfections, various apparatuses for automatic sanitization or sterilization by the use of ultraviolet (UV) irradiation, for example, have been designed and developed. UV radiation of wavelengths at the ultraviolet C (UVC) and ultraviolet B (UVB) ranges are known to be germicidal which work by altering or breaking chemical bonds and/or denaturing proteins and nucleic acids such as DNAs and RNAs of the microorganisms, causing the irradiated microorganisms to be unable to grow and multiply and thus, no longer to be infectious. However, common UV sanitizing apparatuses or installations are known to be bulky and are relatively complex, and thus may not be suitable or convenient for everyday use. The use of UV radiation has also raised concerns in relation to health and safety as studies have shown that UV radiation can be harmful and may cause sunburn, premature skin aging or even skin cancer if subjected to long term exposure.

OBJECTS OF THE INVENTION

An object of the present invention is to provide a novel bag-like container for sterilizing or sanitizing via ultraviolet (UV) irradiation an object accommodated therein.

Another object of the present invention is to mitigate or obviate to some degree one or more problems associated with known sterilizing or sanitizing devices, or at least to provide a useful alternative.

The above objects are met by the combination of features of the main claims. The dependent claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

In a first main aspect, the invention provides a portable bag for sterilizing an object accommodated therein. The bag comprises a flexible body defining an internal space for accommodating the object; a plurality of ultraviolet (UV) radiation emitting means arranged at opposing internal walls of the flexible body; wherein the flexible body comprises one or more layers of fabric materials, with a layer of the one or more layers forming the internal walls comprising a reflective fabric material adapted to reflect ultraviolet (UV) radiation emitted from the UV radiation emitting means and optionally to reflect UV radiation reflected from a surface of the object.

In a second main aspect, the invention provides a method of manufacturing a portable bag for sterilizing an object accommodated therein according to the first aspect. The method comprises providing at least a UV radiation reflective layer material; arranging a plurality of UV radiation emitting means on a surface of the UV radiation reflective layer material; and processing the UV radiation reflective layer material into a flexible bag body, with the surface of the UV radiation reflective layer material forming internal walls of the bag body defining an internal space for accommodating the object; wherein the UV radiation reflective layer material is adapted to reflect UV radiation emitted from the plurality of UV radiation emitting means and optionally to reflect UV radiation reflected from the object.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figures, of which.

DESCRIPTION OF PREFERRED EMBODIMENTS

The following description is of preferred embodiments by way of example only and without limitation to the combination of features necessary for carrying the invention into effect.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

In the claims hereof, any element expressed as a means for performing a specified function is intended to encompass any way of performing that function. The invention as defined by such claims resides in the fact that the functionalities provided by the various recited means are combined and brought together in the manner which the claims call for. It is thus regarded that any means that can provide those functionalities are equivalent to those shown herein.

The present invention relates to a bag or a bag-like container which comprises, in general, a flexible body having one or more closable openings for receiving and accommodating one or more objects. Particularly, but not exclusively, the present invention relates to a portable bag such as a pouch or any flexible, bag-like container capable of sanitizing or sterilizing the accommodated items or objects via ultraviolet (UV) irradiation.

Referring to FIGS. 1 to 7, shown is an embodiment of the present invention provided in the form of a pouch 10. Without being limited to the features as shown in the drawings, the pouch 10 is preferred to comprise a relatively flat configuration where there is at least a pair of opposing longitudinal sides 12a, 12b substantially parallel to each other, and at least a pair of opposing lateral sides 14a, 14b angled but preferably substantially perpendicular to the longitudinal sides 12a, 12b. The pouch 10 may comprise an opening 13 closable or sealable by a suitable closing means 17.

The pouch 10 preferably comprises a flexible body 15, which can be formed of one or more fabric materials, for example. The flexible body 15 defines an internal space or chamber 16 for storing, carrying and/or accommodating one or more items receivable via the opening 13. In one specific embodiment, the pouch 10 preferably has an internal dimension of about 15 cm to about 20 cm in length, about 10 cm to about 15 cm in height, and about 5 cm to about 10 cm in width to allow a useful size of internal space and yet, an effective sterilizing or sanitizing of one or more items or objects received therein.

Preferably, the body 15 of the pouch 10 is configured with a plurality of ultraviolet (UV) radiation emitting means 25 such as, but not limited to, UV light-emitting diodes (LEDs) 25 arranged at opposing internal walls 22a, 22b of the longitudinal sides 12a, 12b of the body 15. The UV LEDs are operable to emit UV radiation at least at the ultraviolet-C (UVC) wavelengths ranging from about 100 nm to about 280 nm for its germicidal effect, and more preferably, ranging from about 260 nm to about 280 nm for its high viral or bacterial DNA absorption and thus most effective sterilization power. Preferably, the ultraviolet (UV) radiation emitting means 25 further comprises UV LEDs capable of emitting ultraviolet B (UVB) and/or ultraviolet A (UVA) radiation. In one embodiment, the pouch 10 may comprise, in addition to the UVC LEDs 25, UVA LEDs adapted to emit UV radiation at a wavelength ranging from about 315 nm to about 400 nm, and more preferably, a wavelength at a near visible range of about 390 nm to about 400 nm for the nearly visible bluish to purplish color to signal the presence, i.e. actuation, of the UV radiation. Alternatively, the pouch 10 can be configured with UV LEDs 25 capable of emitting UV radiation at both the UVC and UVA wavelengths. In one further alternative arrangement, the pouch 10 may comprise one or more visible light emitting means for emitting visible light color to signal the presence of radiation in the internal space 16. The visibility of the radiation is of particular importance to indicate to a user the emission or the presence of UV radiation, which alerts the user to its potentially harmful effects in case of leakage or accidental powering on of the UV LEDs.

Figure 1:
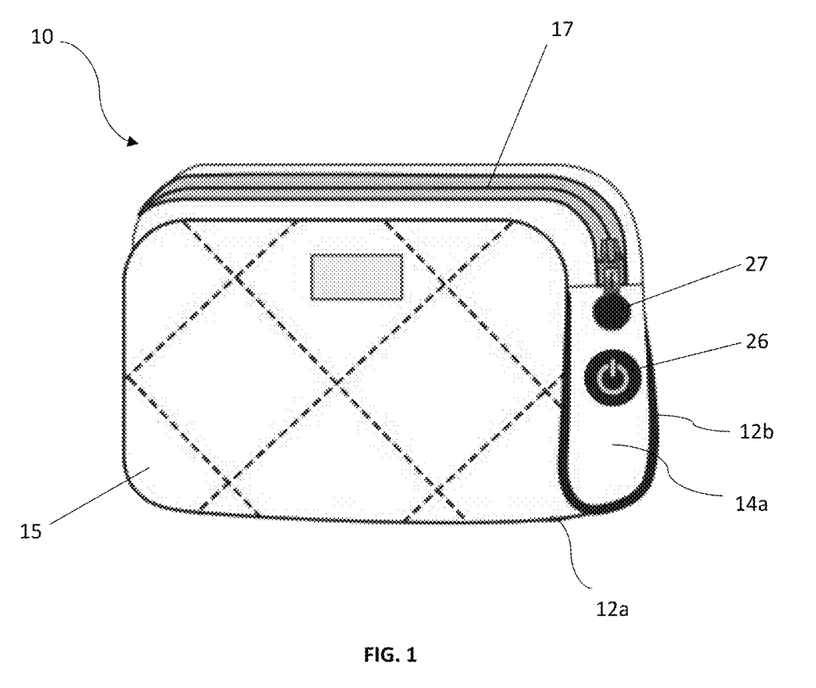
FIG. 1 is a schematic diagram showing a perspective front view of an embodiment of the portable bag in accordance with the present invention.
Figure 2:
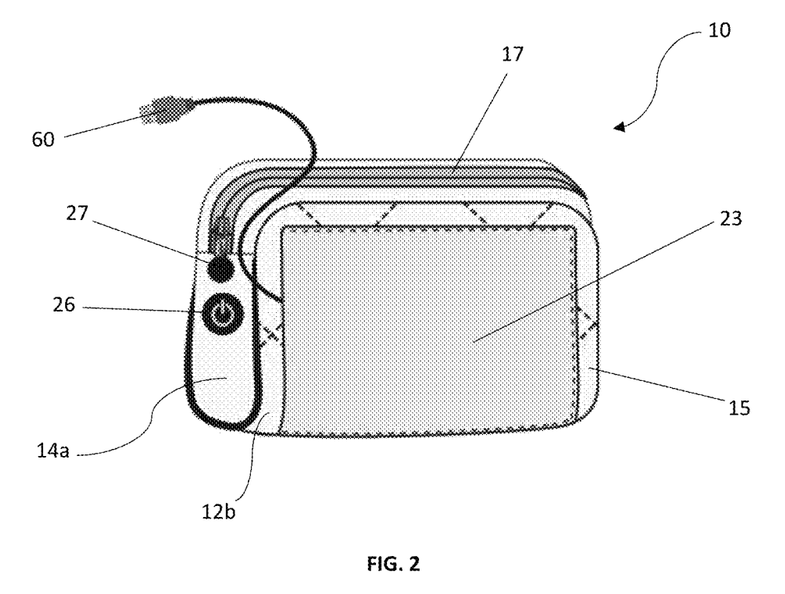
FIG. 2 shows a perspective rear view of the embodiment of FIG. 1.
Figure 3:
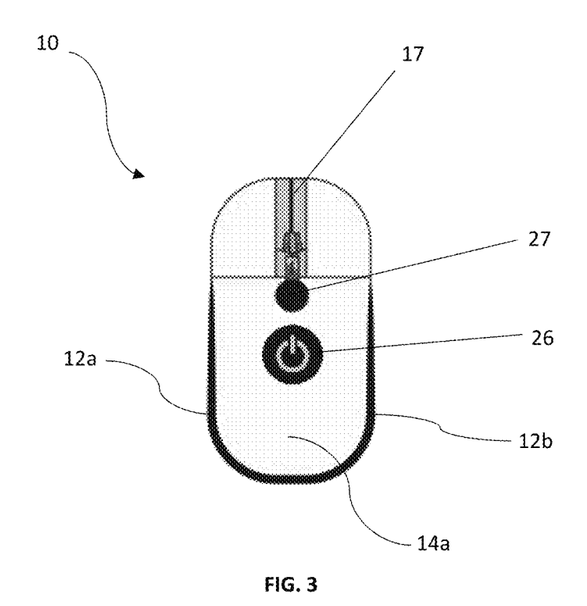
FIG. 3 shows a right side view of the embodiment of FIG. 1.
Figure 4:
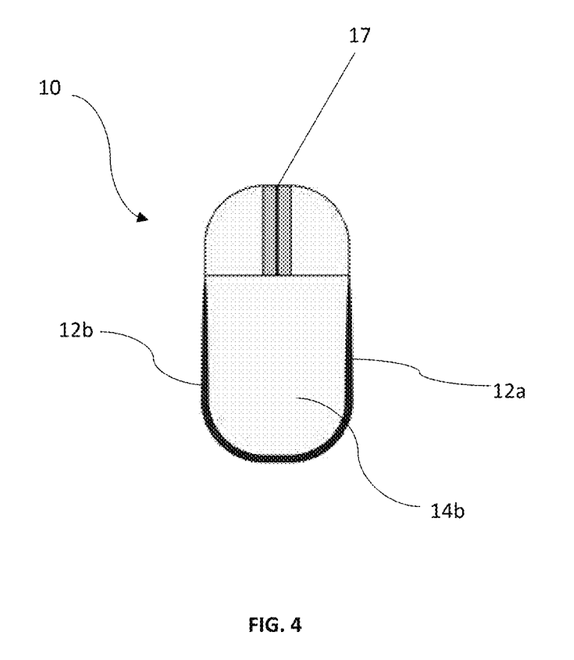
FIG. 4 shows a left side view of the embodiment of FIG. 1.
Figure 5:
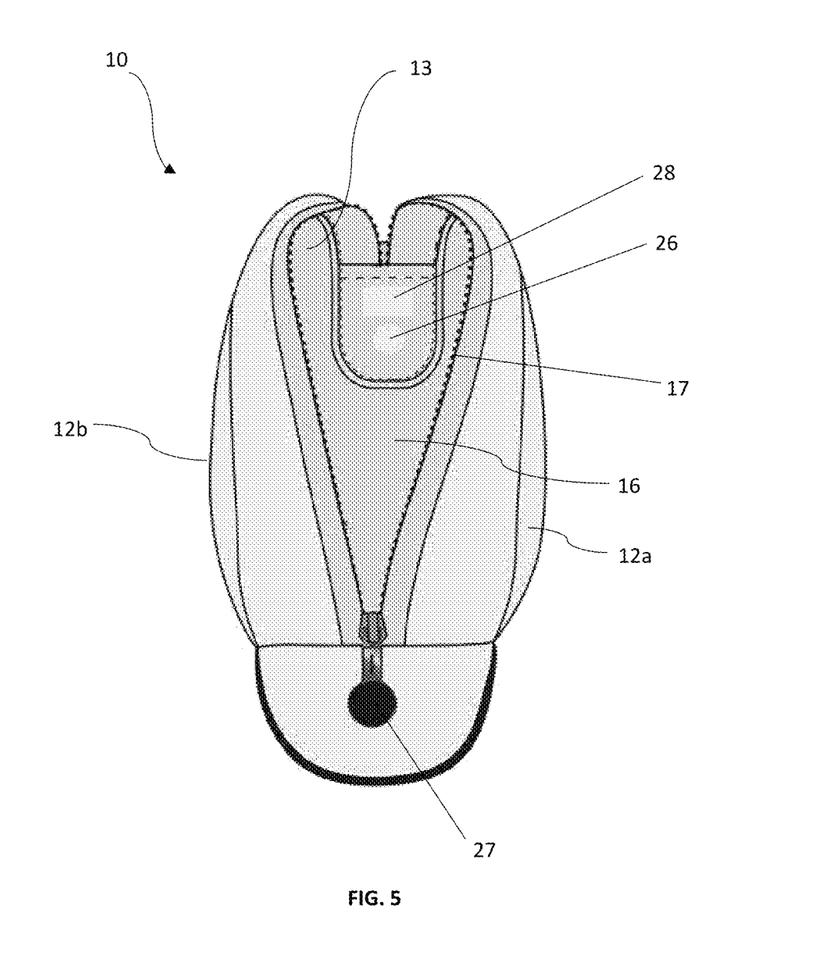
FIG. 5 shows a perspective side view of the embodiment of FIG. 1 with the zip fastener opened.
Figure 6A:
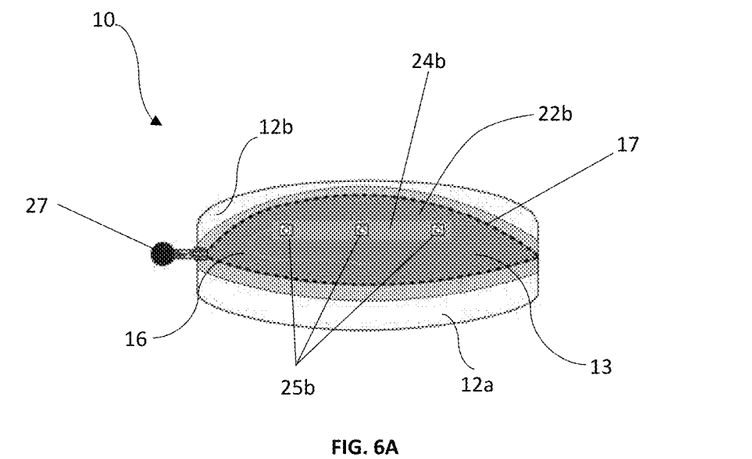
FIG. 6A is a top view of the embodiment of FIG. 5 showing a plurality of UV radiation emitting means on one internal side wall of the portable bag.
Figure 6B:
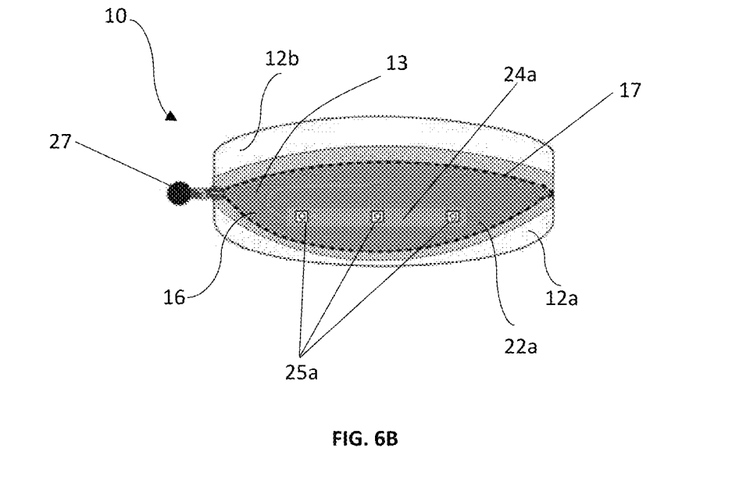
FIG. 6B is the top view of FIG. 6A showing a plurality of UV radiation emitting means provided on an opposing side wall of the portable bag.
Figure 7:
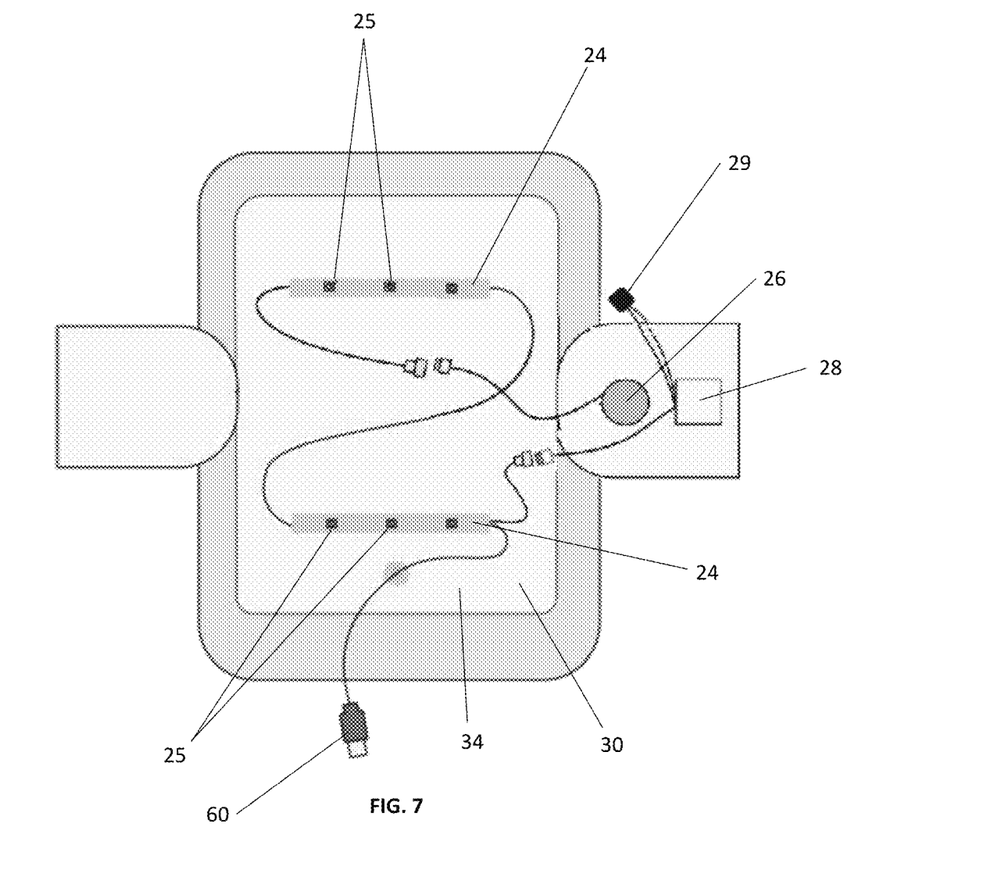
FIG. 7 is an opened plan view showing the internal arrangement of the bag of the embodiment of FIG. 1.

As more clearly shown in FIGS. 6a and 6b, the plurality of UV radiation emitting means 25 may comprise at least three UVC LEDs 25 arranged on each inner facing side of the opposing internal walls 22a, 22b, with the radiation emitting portions facing internally towards the internal space 16 and the thus facing the opposing set of the UVC LEDS 25. The at least three UVC LEDs 25a, 25b on each respective inner facing side of the opposing internal walls 22a, 22b are preferably linearly aligned and/or evenly spaced, as shown in the figures. In one embodiment, the at least three UVC LEDs 25 comprise three evenly spaced UVC LEDs 25a, 25b arranged linearly on each inner facing side of the opposing internal walls 22a, 22b, with the second UVC LED among the three positioned at a substantially centred position along the longitudinal length of the internal walls 22a, 22b. In one specific embodiment, it is preferred for the three UVC LEDs 25 to be spaced evenly at a distance of about 3 cm to 5 cm.

The three UVC LEDs 25 may optionally be arranged on a supporting member 24, which can be configured in the form of rigid strips 24a, 24b. In one embodiment, the strips 24a, 24b may be formed of one or more rigid materials such as fabrics, metals or plastics which are self-supporting. The strips of supporting member 24a, 24b provide a base for mounting and/or supporting the three UVC LEDs 25 and allow a more convenient attachment of the UVC LEDs onto the internal side wall 22a, 22b via sewing or the use of adhesives.

In the embodiment as shown in FIGS. 1 to 7, each of the radiation emitting means 25 is preferred to have a radiating power of about 3 mW to about 10 mW, and more preferably, about 5 mw to about 8 mW. It is further preferred for each of the radiation emitting means 25 to provide a radiating angle of about 100 deg to about 150 deg, and more preferably, about 120 deg.

It will be understood that the UV radiation emitting means 25 and its configuration and arrangement shall not be limited to the embodiments as shown in the figures. Instead, a person skilled in the art will appreciate that any reasonable variations, such as but are not limited to, the number, the size, the power and/or the radiating angle of the UV LEDs, as well as the spacing and spatial arrangement of the UV LEDs, shall also be encompassed by the present invention. This is understandable that the configuration and arrangement of the UV LEDs may vary depending on the application, size and other structural characteristics of the portable bag. For example, a pouch in a larger size may possibly be configured with more than 3 UV emitting means, or that the spacing among the plurality of UV emitting means be increased so as to cover an extended length of the pouch body, or even for the UV LEDs be configured with higher radiating power to thereby increase the strength of the UV radiation emittable.

Figure 8:
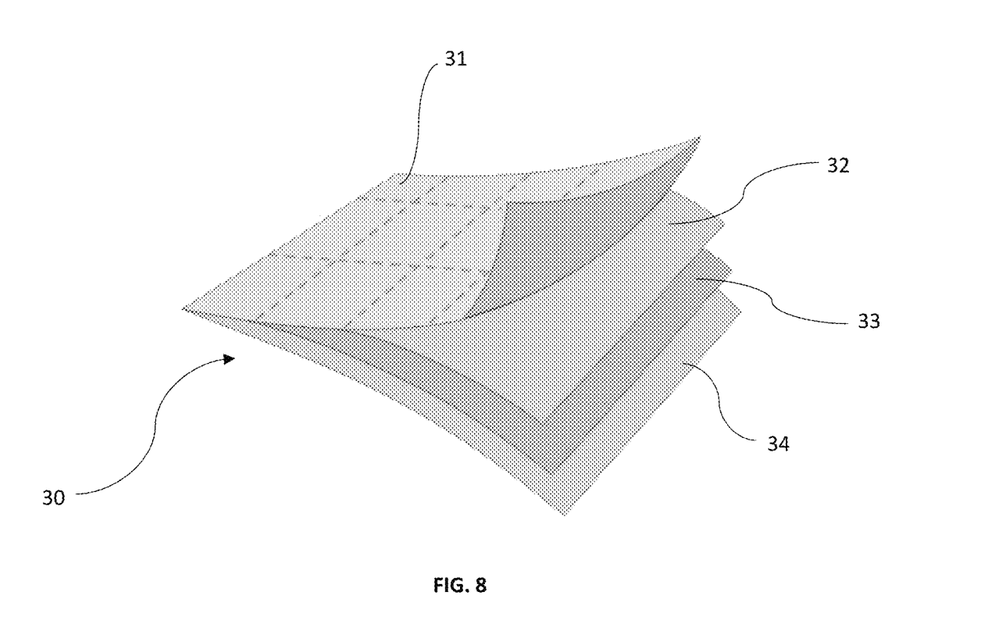
FIG. 8 shows a multiple layers of fabric materials which forms a body of the bag of the embodiment of FIG. 1.

The body 15 of the pouch 10 preferably comprises or is formed of one or more layers of fabric material 30, with the layer or one of said layers which forms the internal walls 22, i.e. the innermost layer 34 as shown in FIG. 8, comprising a UV reflective fabric material adapted to reflect the UV radiation emitted from the UV LEDs 25 as well as any secondary UV radiation reflected from one of more surfaces of the object after being irradiated by the UV LEDs 25. The reflective layer, such as the innermost layer 34 in this example, substantially lines and covers the internal surfaces of the interior of the pouch 10 to provide a UV reflective chamber or interior space 16 which surrounds the object for sterilizing the object. Due to the multi-directional UV reflections which are made possible by the encompassing reflective chamber 16, the strength of UV radiation received by the accommodated object is optimised or significantly enhanced and thus provides a highly effective germicidal effect for sterilizing or sanitizing the content.

In one embodiment, the one or more layers of fabric material 30 preferably comprises multi-layers of fabric materials, which may comprise but are not limited to a four-layered structure as shown in FIG. 8. The four-layered structure may comprise, for example, a first, outermost layer 31 comprising one or more polyester materials such as a polyester woven fabric and more preferably, a recycled polyester woven fabric; a second layer 32 adjacent to the first, outermost layer 31 comprising a filler material which can be one or more of polyester fiberfill, cotton and/or foam materials, for example; a third layer 33 adjacent the innermost reflective layer 31, comprising a UV resistant layer to prevent, reduce or avoid leakage or penetration of UV radiation from the internal space 16—the UV resistant layer may comprise any known UV resisting materials such as nylon and more preferably, a woven nylon fabric; and the fourth, innermost layer 34 comprises one or more UV reflective, metallic materials such as but not limited to, an aluminium fabric, aluminium based fabric or aluminium coated fabric, for example.

As discussed above, the innermost reflective layer 34 which substantially covers surfaces of the internal space 16 of the pouch body significantly optimises and enhances exposure of the germicidal UV radiation experienced by the accommodated object or item and thus provides a highly effective sterilization and sanitization effect. The flexibility of the pouch body 10, as provided and assisted by the multi-layered structure, allows further variations or adjustments to the available reflective distances between the UV radiation emitting means 25, the reflective surface 34 forming internal walls of the reflective internal space 16, as well as surfaces of the accommodated object to be sterilized. This is particularly when the pouch 10 is in use during which the body 15 will be held by the user to vary or to shorten distances between the reflective walls, the UV LEDs and the content. The present invention is thus beneficial in providing a portable reflective chamber or interior space 16, in which UV germicidal irradiation is provided at a highly effective strength onto substantially all surfaces of the object.

In one embodiment, the opening 13 of the pouch 10 is sealable by the closing means 17 which can be provided in the form of a zip fastener as shown in the figures, for example. The closing means 17 preferably comprises or associates with a sealing portion (not shown) which is formed of at least one or more of a UV-resistant material and/or a water-resistant material. The sealing portion can be provided in the form of a small flap of fabric material which assists in preventing or minimising leakage or penetration of UV radiation from the closing means 17.

The pouch 10 may further comprise an actuating means 26 for actuating the UV radiation from the UV radiation emitting means 25. For example, the actuating means 26 may comprise or be provided in the form of one or more of a switch and/or a button arranged externally at the pouch body 15 accessible by the user. In one embodiment, the actuating means 26 may comprise a sensing member 28 for detecting closure of the opening 13 prior to actuation of the UV radiation emitting means 25. For example, the sensing member 28 may comprise a magnetic inductor 28 adapted to allow electric current flow to power the UV LEDs 25 only when the magnetic inductor 28 is activated by at least one of a metallic material and/or a magnetic material. In the embodiment as shown in the figures, the metallic material and/or the magnetic material can be provided in the form of a metallic and/or magnetic zip head 27 of the zip fastener of the closing means 17 which, when the zip fastener is zipped to seal the opening 13, the metallic and/or magnetic zip head 27 is moved from, for example, the lateral side 14b to the lateral side 14a along the zipper track for the metallic zip head 27 be magnetically detectable by the magnetic inductor 28. In one embodiment, the actuating means 26 will become actuatable only when the magnetic inductor 28 is activated, and therefore, the switch and/or the button of the actuating means 26 will only be actuatable by the user to power on the UV LEDs 25 after the zip fastener 17 is sealed and that the magnetic inductor 28 is activated. No UV radiation will be emitted from the UV radiation emitting means 25 if the opening 13 is not properly sealed.

The pouch 10 may optionally be configured with one or more signalling means 29 for generating one or more signals to indicate one or more different usage conditions of the pouch 10. For example, the signalling means 29 can be used to signal whether the pouch 10 is powered up and/or power on, the power level of a rechargeable battery (not shown) of the pouch 10, whether the magnetic inductor 28 is activated, whether the UV LEDs are in use, and/or other faulty or failure operating conditions, etc. The signals generated by the signalling means 29 may comprise one or more of a visible signal, such as light signals from LED lights of one or more colors or light patterns, and/or an audio signal such as beeping in different beeping patterns and/or volume generated by an electronic audio device. In one further embodiment, the rechargeable battery of the pouch 10 is rechargeable by a Universal Serial Bus (USB) 60 connection. In one further embodiment, the pouch 10 may comprise a storage compartment or a pocket 23 preferably arranged at the external, rear longitudinal side 12b of the pouch 10. The pocket 23 is usable for storage of items by the user such as a portable charger.

Figure 9:
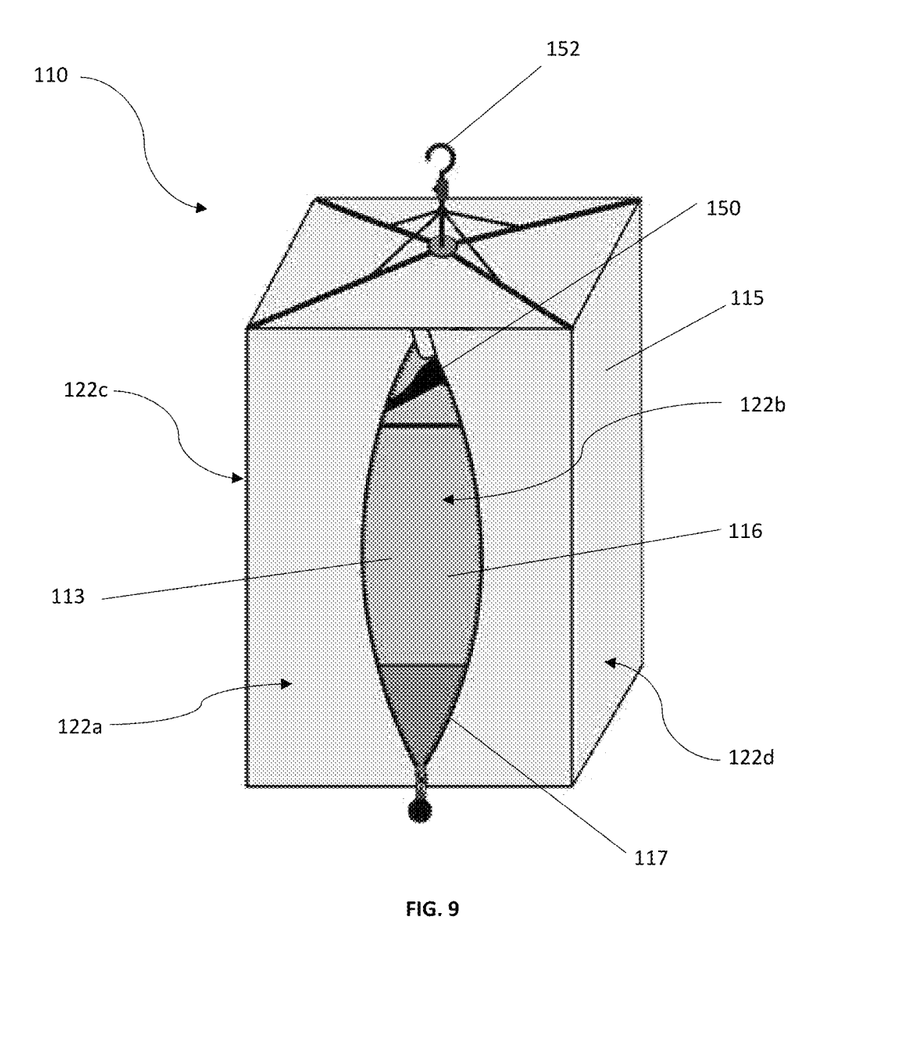
FIG. 9 shows a further embodiment of a flexible bag of the present invention.
Figure 10:
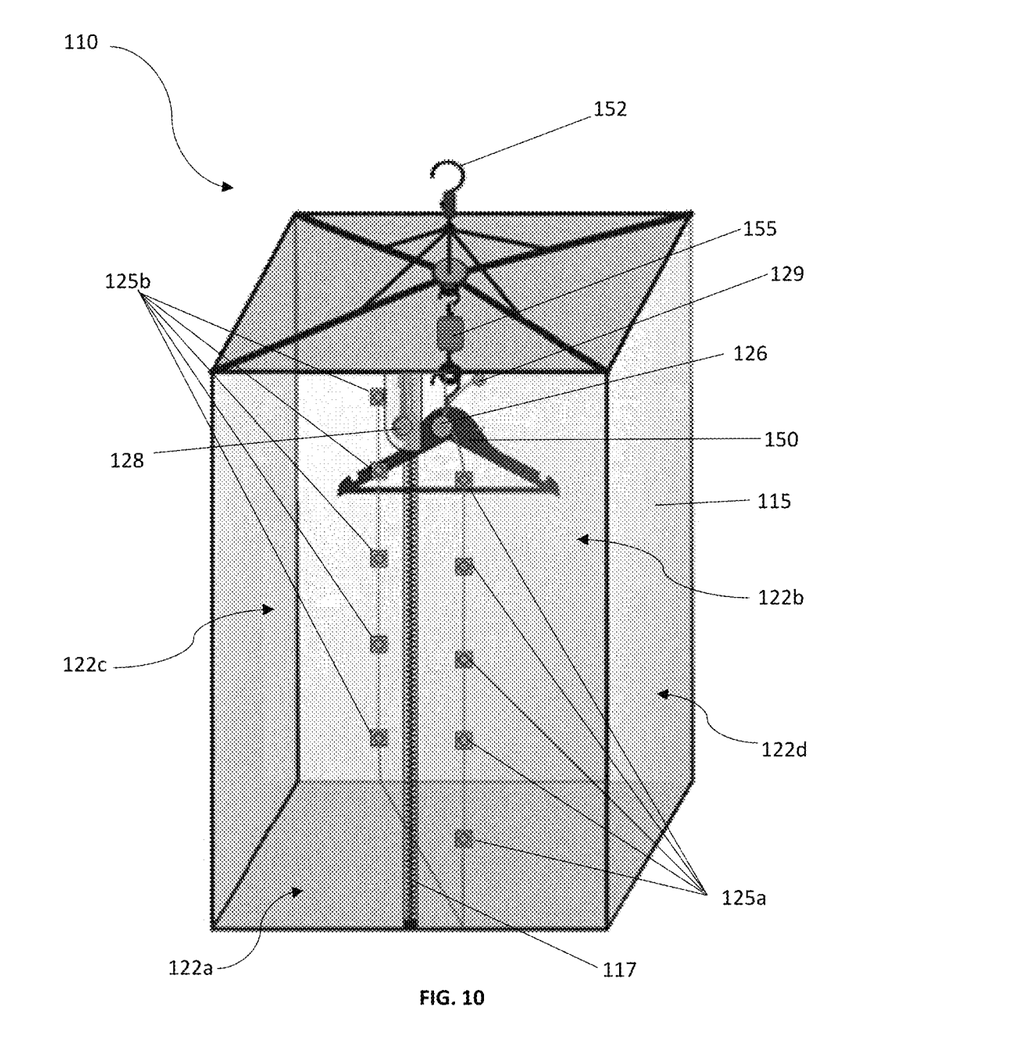
FIG. 10 shows an internal view of the embodiment of FIG. 9.

Referring to FIGS. 9 to 10, shown is a further embodiment of the present invention in which the UV irradiating portable bag is provided in the form of a flexible bag 110 for carrying wearable items such as garment and/or shoes. Similar to the previous embodiments, the garment or shoes bag 110 comprises a flexible body 115 which is formed of the one or more layers of fabric materials. In this embodiment, the body 115 may comprise a 3-layered structure, such as a first, outermost protective layer 131 preferably comprising a water-repelling recycled woven nylon layer; a second layer 133 adjacent to the first, outermost layer preferably comprising a UV resistant, light-blocking material such as a woven nylon layer; and a third, innermost layer 134 comprises one or more UV reflective, metallic materials which can be an aluminium fabric, aluminium based fabric or aluminium coated fabric, for example.

Similar to the embodiment of the pouch 10 previously discussed, the innermost, UV reflective layer 134 of the flexible bag 110 provides a UV reflective internal space or chamber 116 in which the stored items or objects are sterilized or sanitized. Two or more sets of a plurality of UV radiating emitting means 125 can be arranged, preferably in pairs, at two opposing internal side walls 122 such as the longitudinal internal side walls 122a, 122b and/or the lateral internal side walls 122c, 122d, for example. In this embodiment, the plurality of UV radiation emitting means 125 can be provided as five UV LEDs 125 such as UVC LEDs 125 longitudinally aligned and are substantially evenly spaced along the length of the longitudinal internal side walls 122a, 122b, and/or the lateral internal side walls 122c, 122d, for example. In this embodiment, each of the plurality of the UV radiation emitting means 125 preferably has a radiating power of about 10 mW to about 20 mW, with the UV LEDs being spaced evenly at a distance of about 10 cm to about 20 cm, for example. In one further embodiment, the UV radiation emitting means 125 are adapted to emit UV radiation in wavelength at both the UVA and the UVC ranges, which is beneficial in allowing a certain degree of visibility of the radiation emitted.

The innermost reflective layer 134 substantially cover the internal space 116 which facilitates a multi-directional reflection of the germicidal UVC radiations over the enclosed garment or shoe items to be sterilized, which significantly optimises and enhances UV radiation exposure and thus, the sterilization or sanitization effects receivable by the objects. In one embodiment, the flexible bag 110 is preferred to comprise a supporting member 150 for supporting the object inside the body 115, and more preferably, the supporting member 150 can be provided in the form of a hanging means such as a hanger 150 for hanging the object. The hanger 150 may optionally be configured to comprise or be associated with an electric motor 155 which allows motorized rotation of the hanger at a controllable speed and/or direction and thus, a controllable rotation of the items supported at the hanger 150 for an even and all-rounded germicidal UV irradiation over the encased items. The flexible bag 100 may further comprise an external holding means 152 such as a hook 152 as shown in the figures for releasably supporting the bag 100 and/or to facilitate holding of the bag 110 by the user.

In one further embodiment, the bag 110 may also comprise an actuating means 126, such as an externally accessible switch and/or a button for actuating the UV radiation from the UV LEDs 125. In one embodiment, the actuating means 126 may comprise a magnetic inductor 128 for sensing closure of the opening 113 by the zip fastener 117, and more specifically, by detecting the metallic or magnetic zip head 127 of the zip fastener 117 after closure of the opening 113 prior to allowing actuation of the UV LEDs 125. The magnetic inductor 128 works on a similar principle to that of the magnetic inductor 28 of the pouch 10 as previously described and therefore, is not repeated here.

Preferably, the flexible bag 110 is provided with one or more signalling means 129 such as a light-emitting LED and/or an audio emitting device 129 for generating one or more visible and/or audible signals to indicate usage conditions of the bag 110.

The present invention further relates to a method of manufacturing a portable bag for sterilizing a content encased therein. The method comprises the steps of, for example, providing at least a UV radiation reflective layer material; arranging a plurality of UV radiation emitting means at a surface of the UV radiation reflective layer material; and processing the layer material into a flexible bag body, with the surface of the UV radiation reflective layer material forming internal walls of the bag body and defining an internal space for encasing the content; wherein the UV radiation reflective layer material is adapted to reflect UV radiation emitted from the plurality of UV radiation emitting means and also, secondary UV radiation reflected from the content.

Without limited by the specific embodiments described and illustrated, the present invention should not be limited to the pouch and/or garment or shoes bag as embodied, and that a person skilled in the art will understand that any variations as in size and dimension of the portable bag; materials of the portable bag; number of layers and construction of the fabric used; number, type and arrangement of the UV radiation emitting means; number, type and size of the closing means, etc. shall also be encompassed as long as the variations do not depart from the inventive concept of the present invention.

The present description illustrates the principles of the present invention. It will thus be appreciated that those skilled in the art will be able to devise various arrangements that, although not explicitly described or shown herein, embody the principles of the invention and are included within its spirit and scope.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art.

The invention claimed is:

1. A portable bag for sterilizing an object accommodated therein, comprising:
 a flexible body defining an internal space for accommodating the object;
 a plurality of ultraviolet (UV) radiation emitting means arranged at opposing internal walls of the flexible body;
 wherein the flexible body comprises one or more layers of fabric material, with one layer of the one or more layers forming the internal walls comprising a reflective fabric material adapted to reflect ultraviolet (UV) radiation emitted from the UV radiation emitting means and UV radiation reflected from the object;
 a closing means for closing an opening of the flexible body;
 an actuating means adapted to actuate UV radiation from the UV radiation emitting means; wherein the actuating means comprises a magnetic inductor actuatable by a metallic material of the closing means thereby allowing electric current flow to power the UV radiation emitting means only when the magnetic inductor is actuated.

2. The portable bag according to claim 1, wherein the UV radiation emitting means comprise light emitting diodes (LEDs) adapted to emit ultraviolet C (UVC) radiation having a wavelength ranged from about 100 nm to about 280 nm.

3. The portable bag according to claim 2, wherein the LEDs are adapted to emit ultraviolet A (UVA) radiation having a wavelength ranged from about 315 nm to about 400 nm.

4. The potable bag according to claim 2, wherein the plurality of UV radiation emitting means comprise at least three UVC LEDs on each of the opposing internal walls, wherein the at least three UVC LEDs on each of the opposing internal walls are linearly aligned and/or are evenly spaced.

5. The portable bag according to claim 3, wherein the at UVC LEDs comprise three UVC LEDs on each of the opposing internal walls, with a second UVC LED among the three UVC LEDs positioned at a substantially middle position along a longitudinal length of a respective side of the internal walls.

6. The portable bag according to claim 1, wherein each of the radiation emitting means has a radiating power of about 3 mW to about 20 mW.

7. The portable bag according to claim 1, wherein each of the radiation emitting means has a radiating angle of about 100 deg to about 150 deg.

8. The portable bag according to claim 1, wherein the one or more layers of fabric material comprises multi-layers of fabric materials, the multi-layers of fabric materials comprise an innermost layer comprising aluminium fabric, aluminium based fabric or aluminium coated fabric.

9. The portable bag according to claim 8, wherein the multi-layers of fabric material comprise an outermost layer formed of woven polyester fabric.

10. The portable bag according to claim 8, wherein the multi-layers of fabric materials comprise a second layer adjacent the outermost layer, the second layer comprising a filler material.

11. The portable bag according to claim 8, wherein the multi-layers of fabric materials comprise a third layer adjacent the innermost layer, the third layer comprising a UV resistant layer.

12. The portable bag according to claim 1, wherein the closing means comprises a sealing portion formed of at least one of a UV resistant material and a water resistant material.

13. The portable bag according to claim 1, wherein the actuating means comprises one or more of a switch and/or a button.

14. The portable bag according to claim 1, wherein the metallic material of the closing means comprises a zip fastener having a metallic zip head detectable by the magnetic inductor for actuating UV radiation from the UV radiation emitting means.

15. The portable bag according to claim 1, further comprising a signalling means adapted to generate a signal indicating a usage condition of the portable bag wherein the signal comprises one or more of a visible signal and an audio signal.

16. The portable bag according to claim 1, further comprising a supporting member for supporting the object accommodated in the flexible body wherein the supporting member comprises a hanging means for hanging the object in the internal space of the flexible body.

17. The portable bag according to claim 16, wherein the hanging means comprises a rotatable hanger.

18. The portable bag according to claim 17, wherein the rotatable hanger is electrically motorized to effect rotation of the object accommodated within the flexible body.

19. A method of manufacturing a portable bag for sterilizing an object accommodated therein according to claim 1, the method comprising:
 providing at least a UV radiation reflective layer material;
 arranging a plurality of UV radiation emitting means at a surface of the UV radiation reflective layer material;
 processing the UV radiation reflective layer material into a flexible bag body, with the surface of the UV radiation reflective layer material forming internal walls of the bag body defining an internal space for accommodating the object;
wherein the plurality of UV radiation emitting means are arranged at opposing internal walls of the flexible body, and wherein the UV radiation reflective layer material is adapted to reflect UV radiation emitted from the plurality of UV radiation emitting means and UV radiation reflected from the object;
 providing a closing means for closing an opening of the flexible body;
 providing an actuating means adapted to actuate UV radiation from the UV radiation emitting means; wherein the actuating means comprises a magnetic inductor actuatable by a metallic material of the closing means thereby allowing electric current flow to power the UV radiation emitting means only when the magnetic inductor is actuated.

* * * * *